(12) United States Patent
Crank

(10) Patent No.: US 8,876,759 B2
(45) Date of Patent: Nov. 4, 2014

(54) DEVICES, SYSTEMS AND METHODS FOR DELIVERING FLUID TO TISSUE

(75) Inventor: Justin M. Crank, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 13/133,094

(22) PCT Filed: Dec. 4, 2009

(86) PCT No.: PCT/US2009/006381
§ 371 (c)(1),
(2), (4) Date: Jun. 6, 2011

(87) PCT Pub. No.: WO2010/065126
PCT Pub. Date: Jun. 10, 2010

(65) Prior Publication Data
US 2011/0245762 A1    Oct. 6, 2011

Related U.S. Application Data

(60) Provisional application No. 61/120,092, filed on Dec. 5, 2008, provisional application No. 61/122,979, filed on Dec. 16, 2008, provisional application No. 61/122,769, filed on Dec. 16, 2008, provisional application No. 61/155,616, filed on Feb. 26, 2009.

(51) Int. Cl.
*A61M 5/30* (2006.01)
*A61M 5/14* (2006.01)
*A61M 39/10* (2006.01)
A61M 39/00 (2006.01)
A61M 5/145 (2006.01)

(52) U.S. Cl.
CPC ...... *A61M 5/1413* (2013.01); *A61M 2039/0009* (2013.01); *A61M 2205/502* (2013.01); *A61M 2209/045* (2013.01); *A61M 39/10* (2013.01); *A61M 2210/1078* (2013.01); *A61M 2205/505* (2013.01); *A61M 2005/14573* (2013.01); *A61M 5/145* (2013.01)
USPC .......................................................... 604/68

(58) Field of Classification Search
USPC ....................................................... 604/68–70
See application file for complete search history.

(56) References Cited

U.S. PATENT DOCUMENTS 2,607,342 A * 8/1952 Abel .............................. 604/230
3,714,943 A * 2/1973 Yanof et al. ..................... 604/70

(Continued)

FOREIGN PATENT DOCUMENTS

WO    WO9616606 A1    6/1996
WO    WO9736625 A1    10/1997

(Continued)

*Primary Examiner* — Theodore Stigell
(74) *Attorney, Agent, or Firm* — Kagan Binder, PLLC

(57) ABSTRACT

An injection system (200) including an injection chamber (202) and an injectate reservoir (204) that is removably attached to the injection chamber via an intermediate connector (206). The connector extends at a first end from the chamber and terminates at an opposite end with a fitting, such as a luer fitting, to which the injectate reservoir can be attached. The connector can be a relatively flexible component, such as a flexible tube, which is capable of absorbing the energy of an impact or other manipulation of the system to prevent or minimize the possibility of premature disconnection of the reservoir from the system.

17 Claims, 3 Drawing Sheets

(56) References Cited

U.S. PATENT DOCUMENTS

| | | |
|---|---|---|
| 4,093,108 A | 6/1978 | Hein et al. |
| 4,130,119 A | 12/1978 | Sessions et al. |
| 4,596,556 A * | 6/1986 | Morrow et al. ............... 604/70 |
| 4,742,817 A | 5/1988 | Kawashima et al. |
| 4,946,442 A | 8/1990 | Sanagi |
| 5,007,897 A | 4/1991 | Kalb |
| 5,116,313 A | 5/1992 | McGregor |
| 5,261,889 A | 11/1993 | Laine et al. |
| 5,336,178 A | 8/1994 | Kaplan |
| 5,693,016 A | 12/1997 | Gumaste et al. |
| 5,840,062 A | 11/1998 | Gumaste et al. |
| 5,871,462 A * | 2/1999 | Yoder et al. ............... 604/22 |
| 6,068,622 A * | 5/2000 | Sater et al. ............... 604/524 |
| 6,203,533 B1 | 3/2001 | Ouchi |
| 6,210,378 B1 | 4/2001 | Ouchi |
| 6,238,336 B1 | 5/2001 | Ouchi |
| 6,280,413 B1 | 8/2001 | Clark et al. |
| 6,400,980 B1 | 6/2002 | Lemelson |
| 6,537,205 B1 | 3/2003 | Smith |
| 6,547,767 B1 | 4/2003 | Moein |
| 6,641,553 B1 * | 11/2003 | Chee et al. ............... 604/68 |
| 6,905,475 B2 | 6/2005 | Hauschild et al. |
| 7,749,156 B2 | 7/2010 | Ouchi |
| 2003/0163111 A1 | 8/2003 | Daellenbach |
| 2004/0030320 A1 | 2/2004 | Chee et al. |
| 2004/0035491 A1 * | 2/2004 | Castellano ............... 141/27 |
| 2004/0162528 A1 | 8/2004 | Horvath et al. |
| 2005/0192530 A1 | 9/2005 | Castellano |
| 2005/0228225 A1 | 10/2005 | Hauschild et al. |
| 2006/0129125 A1 | 6/2006 | Copa et al. |
| 2006/0264904 A1 * | 11/2006 | Kerby et al. ............... 604/523 |
| 2007/0167921 A1 | 7/2007 | Burren et al. |
| 2007/0225554 A1 | 9/2007 | Maseda et al. |
| 2008/0114203 A1 | 5/2008 | Crank |
| 2008/0119784 A1 | 5/2008 | Roychowdhury |
| 2008/0119823 A1 | 5/2008 | Crank |
| 2009/0124974 A1 | 5/2009 | Crank et al. |
| 2009/0312696 A1 | 12/2009 | Copa et al. |
| 2011/0015614 A1 | 1/2011 | Rykhus, Jr. et al. |
| 2011/0046600 A1 | 2/2011 | Crank |

FOREIGN PATENT DOCUMENTS

| | | |
|---|---|---|
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO2005094921 A1 | 10/2005 |
| WO | WO2006057604 A1 | 6/2006 |
| WO | WO 2006058426 A1 * | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

DEVICES, SYSTEMS AND METHODS FOR DELIVERING FLUID TO TISSUE

CROSS-REFERENCE TO RELATED APPLICATION

This application claims priority to and the benefit of International Application No. PCT/US2009/006381, which in turn claims priority under 35 U.S.C. §119(e) to U.S. Provisional Application No. 61/120,092 (Crank), filed Dec. 5, 2008, titled "Flexible Connection of Injectate Reservoir to Drug Injection System"; U.S. Provisional Application No. 61/122,979 (Crank), filed Dec. 16, 2008, titled "Quick-Connect System for Plunger and Fluid Chamber of Injection Mechanism"; U.S. Provisional Application No. 61/122,769 (Crank), filed Dec. 16, 2008, titled "Non-Wettable Jet Injection Plunger"; and U.S. Provisional Application No. 61/155,616 (Crank), filed Feb. 26, 2009, titled "Bonded Jet Injection Catheter Tube", the entire contents of which are all incorporated herein by reference in their entireties.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example. Needleless devices and methods for treating tissue of the urinary tract are discussed, for example, in Applicants' copending application U.S. Ser. No. 12/087,231, filed Jun. 27, 2008 (Copa et al.), titled "Devices, Systems, and Related Methods for Delivery of Fluid to Tissue", and U.S. Patent Application Publication No. 2006/0129125 (Copa et al.), the entire disclosures of which are incorporated herein by reference. One area of the body in which such needleless fluid delivery systems have been known to be used is for diseases of the prostate, such as prostatitis, benign prostatic hyperplasia, and prostatic carcinoma.

Needleless fluid delivery systems can include the use of a tube-like device, such as an elongated catheter tube, which is configured to provide a jet-injection of a therapeutic fluid at a desired treatment site. Generally, a needleless injector is used to deliver the therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the therapeutic fluid to relatively high pressures.

For any injection or injected tissue, therapeutic agents should be delivered with minimal discomfort and procedure time, and with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery using needleless fluid delivery systems. Such procedures, systems, and components would provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention generally involves needleless fluid injection devices, systems, and methods. These devices and systems allow for targeted delivery of therapeutic fluids at desired anatomical tissue locations, such as locations in the male or female urinary tract, (e.g., bladder, bladder neck, kidney, ureters, urethra, prostate, etc.). The therapeutic fluids can include biologically active species and agents such as chemical and biochemical agents, for example. Exemplary devices can be designed to deliver fluid at various tissue locations, and can further deliver multiple different therapeutic fluids having varying material properties (e.g., viscosity). The devices can be capable of delivering precise amounts of fluid for injection at precise locations and at specific pressures that are adjustable depending on the fluid being administered to the location in the patient.

In one aspect of this invention, an injection system is provided that includes a pressurization or injection chamber and an injectate reservoir that is removably attached to the injection chamber via an intermediate connector. The connector extends at a first end from the chamber and terminates at an opposite end with a fitting, such as a luer fitting, to which the injectate reservoir can be attached. In one particular embodiment, the injectate reservoir comprises a syringe having a cylindrical body, a plunger that is slideably moveable relative to the cylindrical body, and a distal end. When the reservoir is attached to the connector, a quantity of fluid that is contained within the cylindrical body can be transferred to the injection chamber by pressing the plunger toward the distal end until the desired quantity of fluid is ejected from the distal end into the connector. With sufficient fluid pressure, the fluid will then move into a receiving area of the injection chamber. The connector can be a relatively flexible component, such as a flexible tube, which is capable of absorbing the energy of an impact or other intentional or unintentional manipulation of the system to prevent or minimize the possibility of premature disconnection of the reservoir from the system. The size (e.g., length, width, aperture size, etc.) and shape of the connector can vary widely, along with the material from which the connector is made. In one embodiment, the connector is configured to allow an attached reservoir or syringe to have relatively significant range of movement relative to the injection chamber.

In another aspect of the invention, a plunger is provided that is positioned within a channel of a fluid delivery system for delivery of a pressurized fluid. The plunger is used for moving fluid in a fluid chamber through a bore and into an injection chamber. One end of the fluid chamber in which the plunger is positioned includes an O-ring seal or gasket, which is configured to prevent or minimize fluid from leaking out of the chamber and into an adjacent console, for example, and also to allow relatively free movement of the plunger within the chamber. The plunger can also include a O-ring seal or gasket, which is configured to hold pressure in the bore during advancements of the plunger during injection processes. In an exemplary embodiment, the material from which the plunger surface is made can be selected to prevent certain components of the system from coming in contact with the pressurized fluid(s). In particular, the plunger (and/or an outer coating of the plunger) can be made of a material that is not wettable by the injectate, and therefore would be more cleanly wiped off by a seal as it is being withdrawn from an injection chamber.

In another aspect of the invention, a configuration for joining an injection tube to an injection chamber is provided, which minimizes or eliminates leakage and unintentional disconnection of components from each other. In one exemplary embodiment an injection chamber is provided having a channel in which an elongated tube (e.g., catheter tube or shaft) is positioned. The tube is inserted or "wedged" into the channel so that there is no gap or space between the components. In this way, when adhesive is added to the opening or channel adjacent a distal end of the injection chamber, the adhesive flow is generally confined to a predetermined space. That is, the tight fit of the tube within the channel 252 seals off the area in which the adhesive is applied. The end face of the tube can be exposed to the inner area of the channel so that there will be a distributed pressure load on the end face, or an end face of the tube may not be exposed to the inner area of the channel. Thus, in accordance with the invention, the catheter tube may or may not be wedged into a channel of an injection chamber and may or may not butt against a stop or other feature.

In yet another aspect of the invention, a system for attachment of a plunger to a fluid chamber of an injection mechanism is provided. In particular, this embodiment relates to designs that enable the quick connection of a plunger and fluid chamber or injection chamber to a mechanism that actuates the plunger within the fluid chamber to displace the injectate from the fluid chamber.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
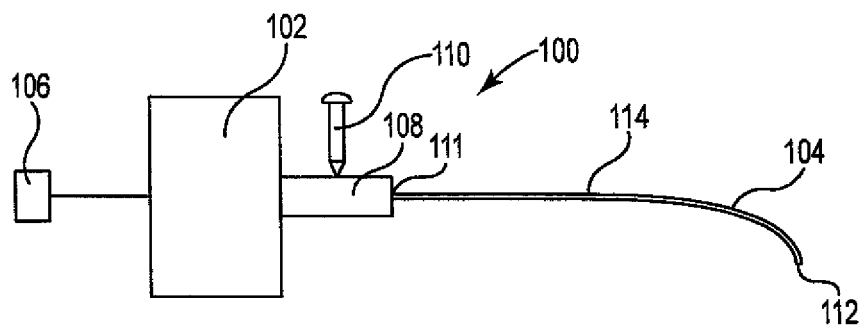
FIG. 1 is a schematic illustration of one embodiment of a needleless fluid delivery system for delivering a therapeutic fluid to a treatment location, in accordance with the invention.

The invention relates to devices and methods useful for injecting fluid into tissue for treatment. The fluid can be injected without the use of a needle and can therefore be referred to as a needleless fluid injection system. Needleless fluid injection systems of the invention can include one or more orifices that deliver fluid in the form of a stream of fluid, which may be referred to as a jet or fluid stream, at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets, without a needle structure passing into the tissue. The type of tissue injected for treatment can be any amenable tissue, which can include tissue at or near the urinary tract (e.g., tissue of the prostate, kidneys, ureters, urethral tissue, bladder (including the bladder neck), etc.), or other tissues such as heart tissue, as desired.

Needleless devices of the type described herein generally include a distal end and a proximal end. As used herein, a "distal end" of a device or system refers to an end area or portion of the device or system that can be introduced internally within a patient's body during a treatment procedure. For example, the elongate shafts or catheters of the needleless injection systems of the invention generally include a distal end that is the first portion of the device that is introduced into the patient for treatment. A distal end may include functional features that operate on fluid or tissue during use, such as one or more ejection orifices, delivery heads (e.g., end effectors, nozzles, etc.) that house one or more ejection orifices, a frictional tissue holding tip, tissue tensioners, lighting or other optical features, steering features, and the like.

As used herein, a "proximal end" of an exemplary needleless device or system is the end that is opposite the distal end of that device or system. It is noted that each individual component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. That is, exemplary needleless fluid delivery devices or systems can include a proximal end that includes a console, and an elongate shaft extending from a proximal end, which is in communication with the console, to a distal end. One or more injection orifices at the distal end can be in fluid communication with the console.

An exemplary console used with systems of the invention can include a housing that connects to or is otherwise (directly or indirectly) in fluid communication with an elongate shaft or catheter tube. The console can include fluid that can be pressurized by a pressure source to cause the fluid to flow through the shaft for injection into tissue at the distal end. A device can eject fluid from one or multiple ejection orifices that can be located at the distal end of the shaft or catheter tube.

Devices, systems, and methods are described herein that can be used to inject a fluid through a surface of a tissue, penetrating without the use of a needle through the tissue surface and into the bulk of the tissue, and dispersing as particles or droplets within the tissue below the tissue surface. The injected fluids may be referred to as an "injectate" or "injection fluid", which may be any type of fluid such as a therapeutic fluid. The injectate can be administered into tissue in a needleless manner, whereby the injectate is delivered as a pressurized fluid stream or jet. This contrasts with injections performed using a needle, whereby a hollow needle structure penetrates tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

Referring now to the Figures, wherein the components are labeled with like numerals throughout the several Figures, and initially to FIG. 1, one preferred configuration of a needleless fluid delivery system 100 is schematically illustrated. Delivery system 100 generally includes an injection console 102, an injection chamber 108 in operative communication with the console 102, and a catheter tube or elongate shaft 104 that is also in operative communication with the console 102. The console 102 includes a user interface 106, which can be used for activating and controlling the activities of the various components of the delivery system 100. The user interface 106 can include an input means for selectively delivering a volume of pressurized fluid through the injection chamber 108. The user interface 106 may further include one or more actuatable devices, such as a foot petal, a hand activated controller, switches, buttons, and/or the like. It is also contemplated that the user interface 106 can include a touch-screen that is capable of receiving touch commands and may optionally include a display system for displaying information such as the mode of operation that is being used and/or certain operating parameters of the system.

Although console 102 can include a wide variety of features, any console used in the fluid delivery systems of the invention can generally include a housing, a pressure chamber, and a pressure source. A console can have any configuration, size, or design, ranging from a small, hand-held component to a relatively larger floor or table-mounted console. The consoles can also include separate or separable components such as a pressure chamber or injection chamber that can be attached, used for an injection procedure, and detached and optionally discarded or sterilized and reused. A shaft or catheter tube can also be attached to a console or a pressure chamber in a manner that facilitates separation and optional re-attachment or disposal.

With separable components, a shaft or injection chamber can be attached to a console housing and used to inject a first patient and/or a first injectate, and then the shaft or pressure chamber can be removed and discarded or sterilized. A second shaft or pressure chamber can then be attached to the console to treat a second patient or the first patient with second injectate or administer another treatment of the first injectate. The second patient or injectate can involve injection and treatment of the same type of tissue as the first patient or injectate, or of a new type of tissue than was treated in the first treatment. In this manner, separable and optionally disposable shaft or pressure chamber components of a needleless injection system can allow a console housing to be used multiple times to inject the same or different injectates to the same or different patients, and to the same or different types of body tissue, thereby providing an injection system that is flexible for use in a wide variety of situations and with a wide variety of fluids. Examples of system configurations, features and combinations of features for disposable, replaceable, and permanent components that can be useful according to the present description are identified in Assignee's U.S. Pat. No. 8,262,605 and in Assignee's following copending patent applications: U.S. Patent Publication Nos. 2009/0312696; 2011/0282318; 2011/0238006; and 2011/0270216, *all* of which are incorporated herein by reference in their *entireties*.

A console can further include actuating features to control distal end features of the system, such as for steering a steerable distal end of a steerable shaft or catheter tube or to actuate ejection of fluid (control fluid or injection fluid). A console can further include actuating features to move a moveable or extendable injection shaft and/or one or more injection orifices or control orifices relative to another shaft component such as a working shaft. A console can further include optional ports to connect a console housing to auxiliary devices, electronics (e.g., control systems), and optical features such as a lens, fiber optic, or electronic viewing mechanism. One or more attachment ports can optionally attach a console to an external and optionally remote component such as an external or remote pressure source, vacuum source, or an external or remote fluid reservoir to supply injectate or control fluid. For example, a console housing may have a fluid port that attaches to a source of a fluid (e,g, injectate or control fluid), to supply the fluid to the console housing, such as to a permanent or detachable pressure chamber. The console can include a pressure chamber and a pressure source capable of pressurizing a fluid contained in the pressure chamber to cause the fluid to flow from the console, through a lumen in the shaft, and then through an ejection orifice as either injectate or a control fluid.

In embodiments of devices that involve the use of a control fluid, a pressurized control fluid can be produced by a console using any useful technique and mechanism. For example, the pressurized control fluid can be produced by a pressure source, such as any pressurized fluid source, magnetohydrodynamic power, expanding steam or gas power, or the like, with any available and useful control fluid, which may be a liquid or a gas.

Fluid can be provided to the system 100 by a fluid supply 110, which can be provided as a syringe that is manually activated, such as by physically pressing a plunger into a syringe barrel that is at least partially filled with fluid to displace fluid from the syringe barrel. Alternatively, fluid supply 110 can have a different configuration than a syringe, and the fluid supply can be automatically or mechanically activated, such as with an electronic fluid supply controller or with one or more remote activation devices that can be manipulated by the user to move the plunger into and out of a syringe barrel. In yet another alternative, the fluid supply 110 is not a syringe, but instead includes a larger fluid source, such as a reservoir or other container that holds the fluid until it is provided to the injection chamber 108. Such a container can be positioned so that the fluid is gravity fed to the injection chamber, for example, or so that the fluid can be extracted using a vacuum source, for another example. With any of the different types of fluid supplies used with the systems of the invention, it is contemplated that an exact amount of fluid to be administered can be premeasured and provided to the system until that quantity of fluid is depleted and/or a predetermined amount of fluid can be extracted from a relatively large fluid supply.

Figure 2:
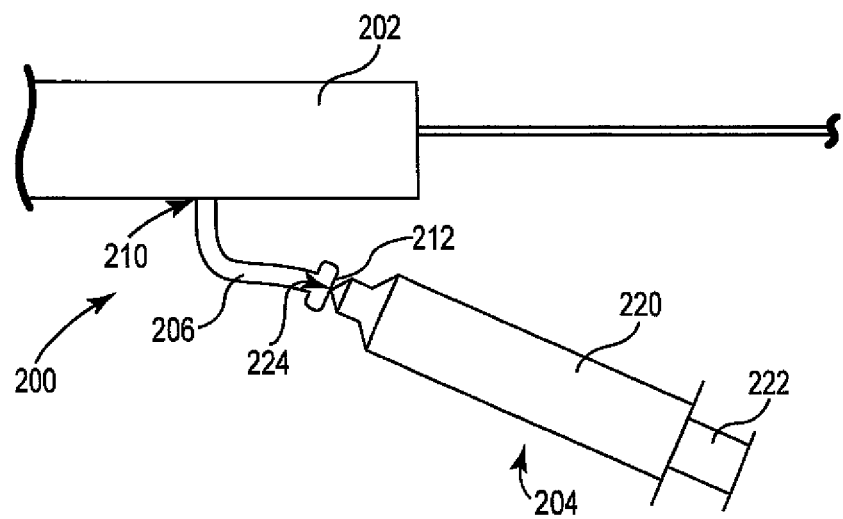
FIG. 2 is a side view of a portion of a fluid delivery system, including a fluid supply device.

Referring additionally to FIG. 2, an embodiment of a connection between a fluid supply and a fluid delivery system 200 in accordance with the invention is shown. In particular, the illustrated portion of delivery system 200 includes a pressurization or injection chamber 202 and an injectate reservoir 204 that is removably attached to the injection chamber 202 via an intermediate connector 206. The connector 206 extends at a first end 210 from the chamber 202 and terminates at an opposite end 212 with a fitting, such as a luer fitting, to which the injectate reservoir 204 can be attached. In one particular embodiment, the injectate reservoir 204 comprises a syringe having a cylindrical body 220, a plunger 222 that is slideably moveable relative to the cylindrical body 220, and a distal end 224. When the reservoir 204 is attached to the connector 206, a quantity of fluid that is contained within the cylindrical body 220 can be transferred to the injection chamber 202 by pressing the plunger 222 toward the distal end 224 until the desired quantity of fluid is ejected from the distal end 224 into the connector 206. With sufficient fluid pressure, the fluid will then move into a receiving area of the injection chamber 202.

Connector 206 can be a relatively flexible component, such as a flexible tube, which is capable of absorbing the energy of an impact or other intentional or unintentional manipulation of the system 202 to prevent or minimize the possibility of premature disconnection of the reservoir 204 from the system. That is, current systems typically only provide for direct, relatively rigid attachment features between a syringe and an injection chamber such that impact or other forces on the syringe cause the direct, relatively rigid attachment features to bend, break, and/or become disconnected from the injection chamber. In any of these situations, transfer of fluid from the syringe to the injection chamber will be interrupted, thereby possibly causing delays to the surgical procedure being performed. In addition, the injectate can leak or otherwise be contaminated when the connection is damaged, thereby causing a loss of a quantity of the injectate. The use of a connector 206, as described herein, can provide for a more secure attachment of components, thereby minimizing the possibilities for the interruption of fluid transfer.

The size (e.g., length, width, aperture size, etc.) and shape of the connector 206 can vary widely, along with the material from which the connector 206 is made. In one embodiment, the connector 206 is configured to allow an attached reservoir or syringe 204 to have relatively significant movement relative to the injection chamber 202. This can be accomplished by making the connector 206 of a relatively flexible, yet strong material, and choosing the length of the connector 206 to be long enough so that the reservoir or syringe 204 can be manipulated by the user without interfering with the other surgical procedures taking place relative to the system 200. In another embodiment, the desired range of movement available for a syringe can be smaller, which may therefore facilitate the use of a shorter and/or more rigid connector 206.

As described above, the connector 206 includes a first end 210 that extends from the chamber 202 and an opposite distal end 212 that includes a fitting, such as a luer fitting, to which the injectate reservoir 204 or syringe can be connected. The first end 210 of connector 206 can be permanently, semi-permanently, or removeably attached to the chamber 202, such as with different types of fittings, clamps, adhesives, threaded connections and the like. To that end, the connector 206 and the chamber 202 can be provided as a system with particularly designed fittings between the two components that prevent leakage but allow for replacement of the connector 206 as necessary or desired. The distal end 212 of connector 206 is provided with a fitting that is adapted for repeatable connection and disconnection of a syringe, such as a luer fitting or any other type of connector end that provides for secure, relatively fluid-tight attachment of a syringe 204 during the process of transferring fluid from the syringe 204. The distal end features can also allow for relatively easy manual connection and disconnection of the syringe 204 from the distal end 212 when desired.

The connector 206 can be made from a wide variety of materials, such as flexible plastics and rubbers (e.g., silicone, nylon, urethane, and the like), which can further be made to have a wide range of flexibilities by changing the geometry of the connector (e.g., cross section, length, and the like). Further, the properties of the connector 206 can be selected to provide a connection component that is capable of absorbing the energy of an impact without adversely affecting the attachment between the components.

A fluid chamber can be a space or volume at a proximal end of a device, such as at a console housing, which can be used to contain pressurized or non-pressurized fluid (e.g., control fluid or injectate). Examples of specific types of fluid chambers include fluid reservoirs and pressure chambers. Optionally, a proximal end of a device may include one or multiple fluid reservoirs and pressure chambers, which can be provided for one or more different fluids including one or more injectates, one or more control fluids, or combinations of injectates and control fluids.

A fluid reservoir is generally a type of fluid chamber that can contain a fluid for a purpose of containing, transferring, holding, or storing a fluid, such as a fixed volume fluid chamber, and may be included as a permanent or removable (i.e., attachable and detachable) component of a console housing.

A pressure chamber or injection chamber can be a type of fluid chamber for containing one or more fluids (e.g., control fluid or injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume for increasing or decreasing the volume (and correspondingly decreasing or increasing pressure) within the variable volume chamber space. Such pressure chambers can include a plunger, piston, bellows, or other mechanisms. A pressure chamber can be pressurized by a pressure source attached to the plunger, bellows, or piston, etc., such that fluid contained in the pressure chamber is ejected under pressure. This pressurized fluid can be used for priming a device and/or for ejecting fluid from an ejection orifice for injection and/or to produce a control force, for example. A pressure source may be any source of energy (e.g., mechanical, electrical, hydraulically derived, pneumatically derived, or the like) such as a spring, solenoid, compressed air, manual syringe, electric power, hydraulic, pneumatic pressure sources, or the like. A pressure chamber may be a permanent or removable (i.e., attachable and detachable) component of a console housing.

Figure 6:
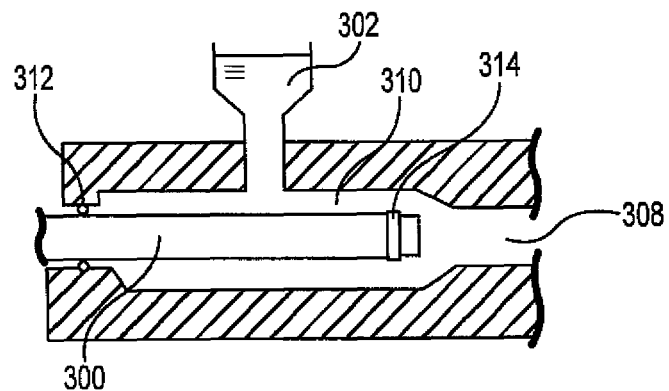
FIG. 6 is a partial cross-sectional view of a portion of a fluid delivery system including a plunger positioned within an injection chamber.

FIG. 6 illustrates an exemplary embodiment of a plunger 300 that is positioned within a fluid chamber 310 of a fluid delivery system of the invention for delivery of a pressurized fluid. The plunger 300 is used for moving fluid in the fluid chamber 310 through a bore 308 of the fluid chamber 310 and into an injection chamber. One end of the fluid chamber 310 in which the plunger 300 is positioned includes an O-ring seal or gasket 312, which is configured to prevent or minimize fluid from leaking out of the chamber 310 and into an adjacent console, for example, and also to allow relatively free movement of the plunger within the chamber 310. The plunger 300 can also include its own O-ring seal or gasket 314, which is configured to hold pressure in the bore 308 during advancements of the plunger 300 during injection processes. It is noted that the o-rings or gaskets 312 and/or 314 can instead be positioned on the opposite surfaces from what is shown. For example, O-ring 312 can be located on the plunger 300 rather than the inside of the chamber 310. However, even with the seal or gasket positioned 312 in the fluid chamber 310, some fluid could possibly still wet onto the surface of the plunger after it is advanced and retracted past the gasket 312. Thus, in accordance with the invention, the material from which the plunger surface is made can be selected to prevent certain components of the system from coming in contact with the pressurized fluid(s).

In particular, the plunger 300 (and/or an outer coating of the plunger 300) can be made of a material that is not wettable by the injectate, and therefore would be more cleanly wiped off by a seal, such as the gasket 312, as it is being withdrawn from an injection chamber. Further, such an arrangement would provide the advantage of eliminating or minimizing contact between the user and any injectates or fluids being used. If the chosen non-wetting material is not mechanically strong or stiff enough to maintain an adequate seal or perform other mechanical duties, the material can be reinforced with one or more additional materials or structures to provide the necessary strength. One such exemplary structure is a hollow, capped tube of non-wettable material that is reinforced with stainless steel. Another exemplary structure is a relatively soft plastic that is reinforced with glass, ceramic and/or nano particles.

Referring again to FIG. 1, a proximal or supply end 111 of the catheter tube or shaft 104 extends from a distal end of the injection chamber 108. The catheter tube 104 may be permanently attached or connected to the injection chamber 108 so that the tube 104 and chamber 108 are provided to the system as a single component. Alternatively, catheter tube 104 may be attachable and detachable from injection chamber 108, such as with quick connection fittings, so that the injection chamber 108 and tube 104 are provided to the system as separate components. Catheter tube 104 further includes a delivery or distal end 112, which is generally opposite the proximal or supply end 111.

Catheter tube or shaft 104 is a generally continuous, elongated tube, which may include multiple lumens, attachments, or other components that may extend along all or part of the length of the tube 104. Catheter tube 104 may further comprise a number of different configurations, such as an endoscope or other catheter configuration, for example. Alternatively, catheter tube 104 can comprise a flexible, elongated tube 114 to allow for easy positioning of the delivery or distal end 112 within the patient. Supply or proximal end 111 of the tube 104 can be generally configured to attach to the injection chamber 108 and can include a quick-connect style connector. Alternatively, the proximal end 111 of the tube 104 can be permanently attached to the injection chamber 108, with one exemplary manner of attachment illustrated in FIGS. 3-5. These arrangements facilitate the joining of a injection tube, which can be subject to relatively high pressures, to an injection chamber in a secure manner that minimizes or eliminates leakage and unintentional disconnection of components from each other.

Figure 3:
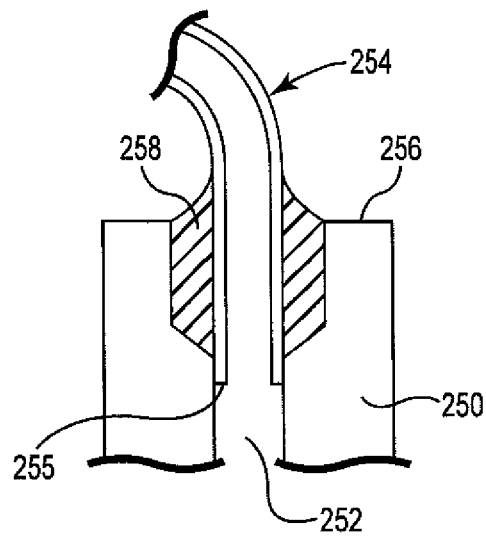
FIG. 3 is a cross-sectional front view of one exemplary embodiment of a connection area between an injection chamber and elongated tube of a fluid delivery system.

In particular, FIG. 3 illustrates one exemplary portion of an injection chamber 250 having a channel 252 in which an elongated tube 254 (e.g., catheter tube or shaft) is positioned. The tube 254 is inserted or "wedged" into the channel 252 so that there is no gap or space between the components. In this way, when adhesive 258 is added to the opening or channel adjacent a distal end 256 of the injection chamber 250, the adhesive flow is generally confined to a predetermined space. That is, the tight fit of the tube 254 within the channel 252 seals off the area in which the adhesive 258 is applied. As illustrated, an end face 255 of the tube 254 is exposed to the inner area of the channel 252, so there will be a distributed pressure load on the end face 255.

Figure 4:
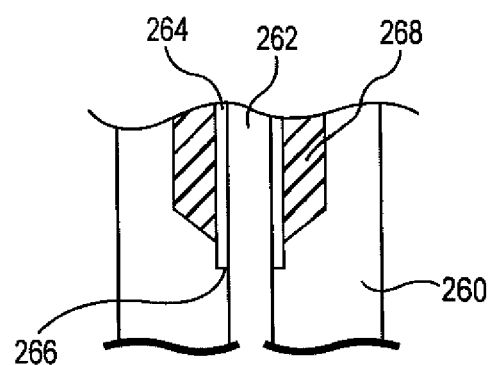
FIG. 4 is a cross-sectional front view of another exemplary embodiment of a connection area of the type illustrated in FIG. 3.

FIG. 4 illustrates a somewhat similar configuration of an injection chamber 260 to that of FIG. 3; however, a tube 264 is pressed into a hole of a channel 262 such that its end face 266 is not exposed to the inner area of the channel. Instead, the hole into which tube 264 is positioned provides a shoulder that blocks the end face 266 of the tube to prevent flow of the adhesive 268 and/or prevents pressure force from building up on the end face 266 of the tube 264. Thus, in accordance with the invention, the catheter tube may or may not be wedged into a channel of an injection chamber and may or may not butt against a stop or other feature.

Figure 5:
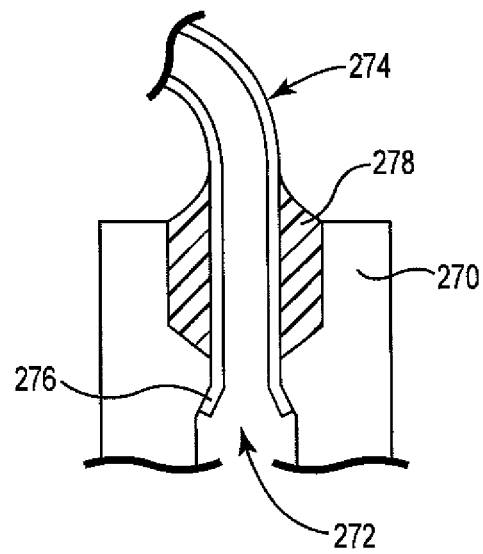
FIG. 5 is a cross-sectional front view of another exemplary embodiment of a connection area of the type illustrated in FIG. 3.

FIG. 5 illustrates yet another embodiment of the arrangement illustrated in FIGS. 3 and 4; however, this embodiment further includes flanges or flares 276 at an end of a tube 274. Tension can be provided to the tube 274 to securely seat or position the flanges 276 within a channel 272 of a chamber 270. In addition, the flanges 276 control the flow of the adhesive 278 when it is applied to the system. In addition, the application of pressure inside the system will provide additional force to seat the flange more securely and help provide a better seal.

Figure 7:
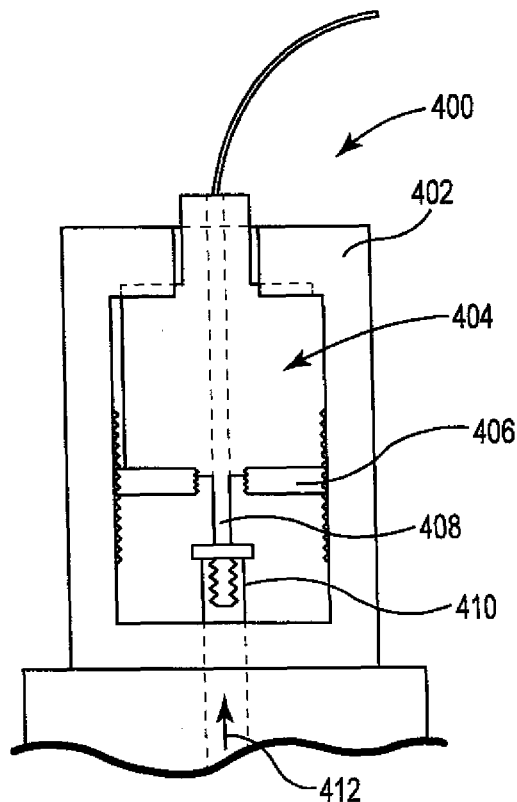
FIG. 7 is a cross-sectional view of a quick connection arrangement for components of a fluid delivery system of the invention.

Another exemplary embodiment of the invention is illustrated in FIG. 7, which provides for attachment of a plunger to a fluid chamber of an injection mechanism. In particular, this embodiment relates to designs that enable the quick connection of a plunger and fluid chamber or injection chamber to a mechanism that actuates the plunger within the fluid chamber to displace the injectate from the fluid chamber. In particular, FIG. 7 illustrates a portion of a fluid delivery system 400 that includes a bracket 402 in which a fluid chamber 404 is positionable. The bracket 402 is threaded internally along at least a portion of its length for engagement with the threads of a tightening nut 406, which is positioned adjacent one end of the fluid chamber 404. As shown, a plunger 408 extends into an end of the fluid chamber 404 and is positioned for engagement with an injection mechanism 410. The injection mechanism 410 can be an air cylinder, solenoid, or the like. As is also illustrated in FIG. 7, the direction of a force is shown by an arrow 412 at the injection mechanism, showing the direction of force to drive the plunger 408 into the fluid chamber 404.

The mechanism illustrated in FIG. 7 can be connected using the following exemplary steps. First, the assembly including the plunger 408 and fluid chamber 404 is placed in the bracket 402 with the plunger 408 in an advanced position and with the tightening nut 406 in a loosened position. Next, the assembly including the plunger 408 and fluid chamber 404 is advanced in an upward direction (relative to the illustration) to seat the fluid chamber 404 in a recession within the bracket 402. This will minimize or prevent the fluid chamber 404 from moving out of slots and windows in the bracket 402 and help maintain proper alignment of the components. Next, the tightening nut 406, which has external threads that are mated with the internal threads of the bracket 402, is tightened against the bottom of the fluid chamber 404. In this way, the fluid chamber 404 is pushed and seated into a recession in the nut 406 that again helps to maintain proper alignment of the components and prevents it from moving out of the slots and windows in the bracket 402. Finally, the plunger 408 is pulled down and screwed into the injection mechanism 410 until firmly seated, which thereby maintains stability of the plunger 408 with respect to buckling. These described connections are provided for suitable alignment of the connection mechanism, plunger, and fluid chamber.

The connection system described above can be modified by eliminating the slot in the bracket, for example. In another variation, the tightening nut described above can be replaced with a spring-loaded tightening ring that would perform the same function. The spring would push up on the tightening ring, which would in turn push up on the fluid chamber. To use this spring-loaded tightening ring, the tightening ring would be pushed down, the fluid chamber would be loaded into the system, and the ring would then be released, thereby allowing it to support the fluid chamber.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A needleless injection system comprising:
an injection chamber;
an elongate shaft extending from the injection chamber, wherein the elongate shaft comprises a distal, fluid distribution end portion;
a connector member comprising a first end that extends directly from the injection chamber, wherein the first end of the connector member is removably attached to the injection chamber;
a syringe comprising a tip that is removably attached to a second end of the connector member; and
a console in fluid communication with the injection chamber, wherein the console comprises a pressure chamber and a pressure source.

2. The needleless injection system of claim 1, wherein the second end of the connector member comprises a luer fitting.

3. The needleless injection system of claim 1, wherein the syringe comprises a cylindrical fluid reservoir and a moveable plunger.

4. The needleless injection system of claim 1, wherein the connector member is relatively flexible.

5. The needleless injection system of claim 4, wherein the connector member is sufficiently flexible to allow movement of the syringe relative to the injection chamber when the syringe is attached to the connector member.

6. The needleless injection system of claim 1, wherein the syringe is capable of absorbing the energy of an impact while maintaining a secure attachment to the connector member.

7. The needleless injection system of claim 1, wherein the injection chamber comprises a fluid chamber and at least one bore.

8. The needleless injection system of claim 7, wherein the bore comprises a cross-sectional area that is smaller than a cross-sectional area of the fluid chamber.

9. The needleless injection system of claim 7 further comprising a plunger that is linearly moveable within the fluid chamber and the at least one bore, and a fluid reservoir containing an injectate.

10. The needleless injection system of claim 9, wherein the fluid reservoir is in fluid communication with the fluid chamber for transfer of injectate from the fluid reservoir to the fluid chamber, and wherein the plunger comprises an outer surface that is not wettable by the injectate.

11. The needleless injection system of claim 10, wherein the non-wettable outer surface of the plunger comprises reinforcement material.

12. The needleless injection system of claim 11, wherein the plunger comprises a hollow, capped tube of non-wettable material and reinforcement material within the hollow portion of the tube.

13. The needleless injection system of claim 1, wherein the injection chamber includes a first end and a second end and wherein the first end of the injection chamber connects to the console and the second end of the injection chamber connects to a supply end of the elongate shaft.

14. A method of performing a needleless injection comprising the steps of:
providing a needless injection system comprising:
an injection chamber;
an elongate shaft extending from the injection chamber, wherein the elongate shaft comprises a distal, fluid distribution end portion;
a connector member comprising a first end that extends directly from the injection chamber, wherein the first end of the connector member is removably attached to the injection chamber;
a syringe comprising a tip that is removably attached to a second end of the connector member; and
a console in fluid communication with the injection chamber, wherein the console comprises a pressure chamber and a pressure source; and
ejecting an injectate from the injection chamber.

15. The method of claim 14, wherein the connector member is flexible.

16. The method of claim 15, wherein the connector member is sufficiently flexible to allow movement of the syringe relative to the injection chamber when the syringe is attached to the connector member.

17. The method of claim 14, wherein the syringe is capable of absorbing the energy of an impact while maintaining a secure attachment to the connector member.

* * * * *